(12) United States Patent
Bastianelli (10) Patent No.: US 9,415,036 B2
(45) Date of Patent: *Aug. 16, 2016

(54) PHARMACEUTICAL COMPOSITION FOR USE IN THE TREATMENT OR PREVENTION OF OSTEOARTICULAR DISEASES

(75) Inventor: Enrico Bastianelli, Rhode-Saint-Genese (BE)

(73) Assignee: BONE THERAPEUTICS, Gosselies (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/867,719

(22) PCT Filed: Feb. 16, 2009

(86) PCT No.: PCT/EP2009/051816
§ 371 (c)(1),
(2), (4) Date: Oct. 20, 2010

(87) PCT Pub. No.: WO2009/101210
PCT Pub. Date: Aug. 20, 2009

(65) Prior Publication Data
US 2011/0027236 A1 Feb. 3, 2011

(30) Foreign Application Priority Data

Feb. 15, 2008 (EP) .................................... 08101683
Jun. 13, 2008 (EP) .................................... 08158284

(51) Int. Cl.
| | |
|---|---|
| *A61P 19/02* | (2006.01) |
| *A61K 31/715* | (2006.01) |
| *A61K 31/4168* | (2006.01) |
| *A61K 9/00* | (2006.01) |
| *A61K 31/728* | (2006.01) |
| *A61K 35/28* | (2015.01) |
| *A61K 35/32* | (2015.01) |
| *A61K 47/36* | (2006.01) |

(52) U.S. Cl.
CPC ............ *A61K 31/4168* (2013.01); *A61K 9/0019* (2013.01); *A61K 31/728* (2013.01); *A61K 35/28* (2013.01); *A61K 35/32* (2013.01); *A61K 47/36* (2013.01)

(58) Field of Classification Search
CPC ............................... A61P 19/02; A61K 31/715
USPC .................................................. 514/16.8, 54
See application file for complete search history.

(56) References Cited

U.S. PATENT DOCUMENTS

| | | | |
|---|---|---|---|
| 6,214,369 B1 | 4/2001 | Grande et al. | |
| 6,331,311 B1 | 12/2001 | Brodbeck et al. | |
| 6,387,413 B1 | 5/2002 | Miyata et al. | |
| 6,503,504 B1 | 1/2003 | Vandenburgh | |
| 6,641,834 B2 | 11/2003 | Olejnik et al. | |
| 6,699,471 B2 * | 3/2004 | Radice et al. | ................ 424/93.7 |
| 2002/0005205 A1 * | 1/2002 | Barry et al. | ................... 128/898 |
| 2003/0022926 A1 | 1/2003 | Lavand'Homme | |
| 2006/0194805 A1 | 8/2006 | Bakthavatchalam et al. | |
| 2007/0042951 A1 | 2/2007 | Olejnik et al. | |
| 2007/0225217 A1 | 9/2007 | Chappell et al. | |

FOREIGN PATENT DOCUMENTS

| | | |
|---|---|---|
| WO | WO 00/17326 | 3/2000 |
| WO | WO 01/80865 A3 | 11/2001 |
| WO | WO 2005/039567 | 5/2005 |
| WO | WO 2006/039704 A2 | 4/2006 |
| WO | WO 2006/092619 A1 | 9/2006 |

OTHER PUBLICATIONS

Lavelle et al. Intra-Articular Injections; Anesthesiology Clinics, vol. 25 (2007) pp. 853-862.*
Girgin et al. Immunomodulatory Effects of Turkish Propolis: Changes in Neopterin Release and Tryptophan Degradation; Immunobiology, vol. 214 (2009) pp. 129-134.*
El-Hashim et al. Anti-Inflammatory and Immunosuppressive Effects of the Enaminone E121; European Journal of Pharmacology, vol. 632 (2009) pp. 73-78.*
Bocelli-Tyndall et al., "Bone marrow mesenchymal stromal cells (BM-MSCs) from healthy donors and auto-immune disease patients reduce the proliferation of autologous- and allogenic-stimulated lymphocytes in vitro," *Rheumatology* (2007) 46: 403-408.
Cook-Mills et al., "Inhibition of lymphocyte activation by catecholmaines: evidence for a non-classical mechanism of catecholamine action," *Immunology* (1995) 85: 544-549.
Bondeson et al., "The role of synovial macrophages and macrophage-produced cytokines in driving aggrecanases, matrix metalloproteinases, and other destructive and inflammatory responses in osteoarthritis," *Arthritis Research & Therapy* (2006) 8: R187: 1-12.
Yamawaki et al., "Hyaluronan receptors involved in cytokine induction in monocytes," *Glycobiology* (2009) 19 (1): 83-92.
Pelletier et al., "Osteoarthritis, an inflammatory disease," *Arthritis & Rheumatism* (2001) 44 (6): 1237-1247.
Mchugh et al., "The immunosuppressive drug thalidomide induces T helper cell type 2 (Th2) and concomitantly inhibits Th1 cytokine production in mitogen- and antigen-stimulated human peripheral blood mononuclear cell cultures," *Clin. Exp. Immunol.* (1995) 99: 160-167.
Le Blanc et al., "Mesenchymal stem cells inhibit and stimulate mixed lymphocyte cultures and mitogenice responses independently of the major histocompatibility complex," *Scandinavian Journal of Immunology* (2003) 57: 11-20.
Levesque et al., "Activated T lymphocytes regulate hyaluronan binding to monocyte CD44 via production of IL-2 and IFN-{{gamma}}," *The Journal of Immunology* (2001) 166: 188-196.

(Continued)

*Primary Examiner* — Kagnew H Gebreyesus
*Assistant Examiner* — Paul Martin
(74) *Attorney, Agent, or Firm* — Merchant & Gould P.C.

(57) ABSTRACT

A pharmaceutical composition for the acute and/or chronic treatment or prevention of osteoarticular diseases includes an adequate pharmaceutical carrier or diluent, a polysaccharide and/or a glycosaminoglycan, an anti-inflammatory agent and stem cells.

12 Claims, 1 Drawing Sheet

(56) References Cited

OTHER PUBLICATIONS

Ozturk et al., "The safety and efficacy of intraarticular hyaluronan with/without corticosteroid in knee osteoarthritis: 1-year, single-blind, randomized study," *Rheumatol. Int.* (2006) 26: 314-319.

Beresford et al., "The effects of dexamethason and 1,25-Dihydroxyvitamin $D_3$ on osteogenic differentiation of human marrow stromal cells In Vitro," *Archs. Oral. Biol.* (1994) 39 (11): 941-947.

Alagol et al., "Intraarticular analgesia after arthroscopic knee surgery: comparison of neostigmine, clonidine, tenoxicam, morphine and bupivacaine," *Knee Surg. Sports Traumatol. Arthrosc.* (2005) 13: 658-663.

Gupta, A., "Update on intra-articular analgesia," *Techniques in Regional Anesthesia and Pain Management* (2003) 7 (3): 155-160.

Derfoul et al., "Glucocorticoids promote chondrogenic differentiation of adult human mesenchymal stem cells by enhancing expression of cartilage extracellular matrix genes," *Stem Cells* (2006) 24 (6): 1487-1495.

Barbucci et al., "Hyaluronic acid hydrogel added with ibuprofen-lysine for the local treatment of chondral lesions in the knee: In Vitro and In Vivo investigations," *Journal of Biomedical Materials Research* (2005) 75B (1): 42-48.

Ringe et al., "Future of tissue engineering in rheumatic diseases," *Expert Opin. Biol. Ther.* (2007) 7 (3): 283-287.

Murphy et al., "Stem cell therapy in a caprine model of osteoarthritis," *Arthritis & Rheumatism* (2003) 48 (12): 3464-3474.

Rubin, B., "Management of osteoarthritic knee pain," *JAOA* (2005) Supplement 4, vol. 105, No. 9: S23-S28.

Lo et al., "Intra-articular hyaluronic acid in treatment of knee osteoarthritis," *JAMA* (2003) 290 (23): 3115-3121.

Wang et al., "Therapeutic effects of hyaluronic acid on osteoarthritis of the knee," *The Journal of Bone and Joint Surgery* (2004) 86-A (3): 538-545.

Gerwin et al., "Intraarticular drug delivery in osteoarthritis," *Advanced Drug Delivery Reviews* (2006) 58: 226-242.

Buerkle et al., "Thermal and mechanical antinociceptive action of spinal vs peripherally administered clonidine in the rat inflammed knee joint model," *British Journal of Anasthesia* (1999) 83 (3): 436-41.

Ansah et al., "Peripheral suppression of arthritic pain by intraarticular fadolmidine, an α2-Adrenoceptor Agonist, in the rat," *Pain Mechanisms* (2007) 105 (1): 245-250.

Grecomoro et al., "Therapeutic synergism between hyaluronic acid and dexamethasone in the intra-articular treatment of osteoarthritis of the knee: a preliminary open study," *Current Medical Research and Opinion* (1992) 13 (49): 49-55.

Kolarz et al., "Long-term benefits and repeated treatment cycles of intra-articular sodium hyaluronate (Hyalgan) in patients with osteoarthritis of the knee," *Seminars in Arthritis and Rheumatism* (2003) 32 (5): 310-319. XP002489507.

Wang et al., "Therapeutic effects of hyaluronic acid on osteoarthritis of the knee," *The Journal of Bone and Joint Surgery* (2004) 86-A: 538-545. XP002489510.

Stitik et al., "Efficacy and safety of hyaluronan treatment in combination therapy with home exercise for knee osteoarthritis pain," *Arch Phys Med Rehab II* (2007) 88: 135-141. XP002525191.

Joshi et al., "Postoperative analgesia for outpatient arthroscopic knee surgery with intraarticular clonidine and/or morphine," *Anasth. Analg.* (2000) 90L 1102-1106. XP002489506.

Arrich et al., "Intra-articular hyaluronic acid for treatment of osteoarthritis of the knee: systematic review and meta-analysis," *CMAJ* (2005) 172 (8): 1-13.

Fernandez Lopez et al., "Efficacy and safety of intararticular hyaluronic acidin the treatment of hip osteoarthritis: a systematic review," *OsteoArthritis and Cartilage* (2006) 14: 1306-1311.

Uthman et al., "Intra-articular therapy in osteoarthritis," *Postgrad Med. J.* (2003) 79: 449-453.

Gentili et al., "Postoperative analgesia by intraarticular clonidine and neostigmine in patients undergoing knee arthroscopy," *Regional Anesthesia and Pain Medicine* (2001) 26 (4): 342-347. XP002489503.

Qvistgaard et al., "Intra-articular treatment of hip osteoarthritis: a randomized trial of hyaluronic acid, corticosteroid, and isotonic saline," *Osteoarthritis and Cartilage* (2006) 14: 163-170.

Zouher et al., "Addition of clonidine and fentanyl: comparison between three different regional anesthetic techniques in circumcision," *Pediatric Anesthesia* (2005) 15: 964-970.

Reuben et al., "Intravenous regional anesthesia using lidocaine and clonidine," *Anesthesiology* (1999) 91: 654-658.

Xu et al., "Anti-hypertensive drugs alter cytokine production from preeclamptic placentas and peripheral blood mononuclear cells," *Hypertension in pregnancy* (2007) 26: 343-356.

Gentili et al., "Peripheral analgesic effect of intra-articular clonidine," *Pain* (1996) 593-596.

Luiz-Cleber et al., "The antinociceptive effect of local or systemic parecoxib combined with lidocaine/clonidine intravenous regional analgesia for complex regional pain syndrome Type I in the arm," *Anesth. Analg.* (2005) 101: 807-811.

Murphy et al., "A non-surgical approach to low back pain," *Medecine and Health* (2000) 83 (4): 104-107.

Bellamy et al., "Intraarticular corticosteroid for treatment of osteoarthritis of the knee (Review)," *The Cochrane Collaboration* (2006) 2: 1-213.

Armand et al., "Meta-analysis of the efficacy of extradural clonidine to relieve postoperative pain: an impossible task," *British Journal of Anasethesia* (1998) 81: 126-134.

Barron et al., "Managing Osteoarthritic knee pain," *JAOA* (2007) 6 (107): ES21-ES27.

Nishiyama et al., "The synergistic interaction between midazolam and clonidine in spinally-mediated analgesia in two different pain models of rats." *Anesth. Analg.* Oct. 1993 (4): 1025-1031, (2001).

Chang et al., "Effects of non-steroidal anti-inflammatory drugs on cell proliferation and death in cultured epiphyseal-articular chondrocytes of fetal rats", Toxicology 228 (2006), p. 111-123.

Brandt, "Effects on Nonsteroidal Anti-Inflammatory Drugs on Chondrocyte Metabolism in Vitro and in Vivo", The American Journal of Medicine (1987), vol. 83 (suppl 5A), p. 29-34.

Arend et al., "Inhibition of the production and effects of interleukin-1 and tumor necrosis factor α in rheumatoid arthritis", *Arthritis & Rheumatism*, vol. 38, No. 2, 1995, p. 151-160.

Augello et al., "Cell Therapy Using Allogeneic Bone Marrow Mesenchymal Stem Cells Prevents Tissue Damage in Collagen-Induced Arthritis", *Arthritis & Rheumatism*, vol. 56, No. 4, 2007, p. 1175-1186.

Chorąży-Massalska et al., "The effect of taurine chloramine on pro-inflammatory cytokine production by peripheral blood monoculear cells isolated from rheumatoid arthritis and osteoarthritis patients", *Clinical and Experimental Rheumatology*, 2004, 22: 692-698.

Doronzo et al., 2006, "In Vitro Testing for Antiinflammatory Properties of Compounds", *Clinical Chemistry* 52, No. 6, p. 1201-1202.

Firestein, "Evolving concepts of rheumatoid", *Nature*, vol. 423, 2003, www.nature.com/nature.

Gerards et al., "Inhibition of cytokine production by methotrexate", *Rheumatology*, 2003, 42:1189-1196.

Jenny et al., 2011, "In vitro testing for anti-inflammatory properties of compounds employing peripheral blood mononuclear cells freshly isolated from healthy donors", *Inflamm. Res.*, 60:127-135.

Ribel-Madsen et al., "A Synoviocyte Model for Osteoarthristis and Rheumatoid Arthristis: Response to Ibuprofen, Betamethasone, and Ginger Extract—A Cross-Sectional In Vitro Study", *Arthritis*, vol. 2012, Article ID 505842, 9 pages.

Richard et al., "Pro-inflammatory effects of the aminobisphosphonate ibandronate in vitro and in vivo", *Rheumatology*, 1999, 38:984-991.

Zheng et al., "Therapeutic effects of standardized *Vitex negundo* seeds extract on complete Freund's adjuvant induced arthritis in rats," Phytomedicine 21 (2014) pp. 838-846.

Cutolo, "Effects of DMARDs on IL-Ra levels in rheumatoid arthritis: is there any evidence?," Clinical and Experimental Rheumatology (2002), pp. S26-S31.

Sennikov et al., "Expression of TNFa membrane-bound receptors in the peripheral blood mononuclear cells (PMBC) in rheumatoid arthritis patients," Cytokine 73 (2015) pp. 288-294.

(56) References Cited

OTHER PUBLICATIONS

Herrero-Beaumont et al., "Effect of chondroitin sulphate in a rabbit model of atherosclerosis aggravated by chronic arthritis," British Journal of Pharmacology (2008), pp. 843-851.

Tat et al., "The differential expression of osteoprotegerin (OPG) and receptor activator of nuclear factor κB ligand (RANKL) in human osteoarthritic subchondral bone osteoblasts is an indicator of the metabolic state of these disease cells," Clinical and Experimental Rheumatology (2008), pp. 295-304.

Amiable et al., "Proteinase-activated receptor (PAR)-2 activation impacts bone resorptive properties of human osteoarthritic subchondral bone osteoblasts," Bone 44 (2009), pp. 1143-1150.

Remacha et al., "Expression of genes involved in immune response and in vitro immunosuppressive effect," Veterinary Immunology and Immunopathology, (2015), pp. 107-118.

Li et al., "Levels of Metalloproteinase (MMP-3, MMP-9), NF-kB Ligand (RANKL), and Nitric Oxide (NO) in Peripheral Blood of Osteoarthritis (OA) Patients," Clin. Lab, (2012), pp. 755-762.

Alijotas-Reig et al., "Bioengineered hyaluronic acid elicited a nonantigenic T cell activation: Implications from cosmetic medicine and surgery to nanomedicine," Wiley Periodicals, Inc., (2010), pp. 180-190.

Neurauter et al., "Atorvastatin suppresses interferong-induced neopterin formation and tryptophan degradation in human peripheral blood mononuclear cells and in monocytic cell lines," Clin Exp Immunol (2003); 131:264-267.

Winkler et al., "In Vitro Testing for Anti-inflammatory Properties of Compounds," Clinical Chemistry 52, No. 6, (2006); 1201-1202.

Wirleitner et al., "Resveratrol suppresses interferon-_-induced biochemical pathways in human peripheral blood mononuclear cells in vitro," Immunology Letters 100 (2005); 159-163.

Zvetkova et al., "Aqueous extracts of Crinum latifolium žL./ and Camellia sinensis show immunomodulatory properties in human peripheral blood mononuclear cells," International Immunopharmacology 1 (2001); 2143-2150.

* cited by examiner

PHARMACEUTICAL COMPOSITION FOR USE IN THE TREATMENT OR PREVENTION OF OSTEOARTICULAR DISEASES

This application is a National Stage Application of PCT/EP2009/051816, filed Feb. 16, 2009, which claims benefit of Ser. No. 08158284.3, filed Jun. 13, 2008 in the EPO, and also of Ser. No. 08101683.4, filed Feb. 15, 2008 in the EPO which applications are incorporated herein by reference. To the extent appropriate, a claim of priority is made to each of the above disclosed applications.

FIELD OF THE INVENTION

The present invention is in the pharmaceutical field and is related to a new pharmaceutical composition for use in the treatment or the prevention of the acute and/or chronic osteoarticular diseases.

BACKGROUND OF THE INVENTION

Osteoarthritis, the most common form of arthritis, is a disease characterised by a slow degenerative processes in the articular cartilage, subchondral bone associated with marginal osteophyte formation, and low grade inflammation. Osteoarthritis is believed to affect 15% of the population in its chronic form. Of those, one-quarter are severely disabled. Most cases of osteoarthritis have no known cause and are referred to as primary osteoarthritis. When the cause of the osteoarthritis is known, the condition is referred to as secondary osteoarthritis. Secondary osteoarthritis is caused by another disease or condition. Conditions that can lead to secondary osteoarthritis include repeated trauma or surgery to the joint structures, abnormal joints at birth (congenital abnormalities), gout, diabetes, and other hormone disorders. Other forms of arthritis are systemic illnesses, such as rheumatoid arthritis and systemic lupus erythematosus (SLE).

Osteoarthritis involves mainly the hips, knees, spine, and the interphalangeal joints. The most common symptom of osteoarthritis is pain in the affected joint(s) after repetitive use. Joint pain is usually worse later in the day. There can be swelling, warmth, and creaking of the affected joints. Pain and stiffness of the joints can also occur after long periods of inactivity. In severe osteoarthritis, complete loss of cartilage cushion causes friction between bones, causing pain at rest or pain with limited motion.

Osteoarthritis is characterized by a slow degradation of cartilage over several years. In normal cartilage, a delicate balance exists between matrix synthesis and degradation; in osteoarthritis, however, cartilage degradation exceeds synthesis. The balance between synthesis and degradation is affected by age and is regulated by several factors produced by the synovium and chondrocytes, including cytokines, growth factors, aggrecanases, and matrix metalloproteinases. In addition to water, the extracellular matrix is composed of proteoglycans, made up of glycosaminoglycans attached to a backbone made of hyaluronic acid, entrapped within a collagenous framework or fibrillary matrix. A significant proteoglycal in articular cartilage is aggrecan, which binds to hyaluronic acid and helps provide the compressibility and elasticity of cartilage. Aggrecan is cleaved by aggrecanases, leading to its degradation and to subsequent erosion of cartilage. The loss of aggrecan from the cartilage matrix is one of the first pathophysiological changes observed in OA.

Cytokines produced by the synovium and chondrocytes, especially IL-1beta and Tumor Necrosis Factor alpha (TNF-alpha), are also key players in the degradation of cartilage. IL-1beta is spontaneously released from cartilage of osteoarthritis but not normal cartilage. Both IL-1beta and TNF-alpha stimulate their own production and the production of other cytokines (e.g., IL-8, IL-6, and leukotriene inhibitory factor), proteases, and prostaglandin $E_2$ ($PGE_2$). Synthesis of the inflammatory cytokines IL-1beta and TNF-alpha and expression of their receptors are enhanced in osteoarthritis. Both cytokines have been shown to potently induce degradation of cartilage in vitro. Other proinflammatory cytokines overexpressed in osteoarthritis include IL-6, IL-8, IL-11, and IL-17, as well as leukotriene inhibitory factor.

The extracellular matrix (ECM) composing the cartilage is degraded by locally produced matrix metalloproteinases. Proinflammatory cytokines, including IL-1beta, TNF-alpha, IL-17, and IL-18, increase synthesis of matrix metalloproteinases, decrease matrix metalloproteinase enzyme inhibitors, and decrease extracellular matrix synthesis.

In an attempt to reverse the breakdown of the extracellular matrix, chondrocytes increase synthesis of matrix components including proteoglycans. Even though this activity increases, a net loss of proteoglycans in the upper cartilage layer is seen. Elevated anti-inflammatory cytokines found in the synovial fluid of osteoarthritis include IL-4, IL-10, and IL-13. Their role is to reduce production of IL-1beta, TNF-alpha, and matrix metalloproteinases, and inhibit prostaglandin release. Local production of growth and differentiation factors such as insulin-like growth factor 1, transforming growth factors, fibroblastic growth factors, and bone morphogenetic proteins also stimulate matrix synthesis.

STATE OF THE ART

Currently available pharmacological therapies target palliation of pain and include analgesics (i.e. acetaminophen, cyclooxygenase-2-specific inhibitors, non-selective nonsteroidal anti-inflammatory drugs, tramadol, opioids). However, the clinical presentation of osteoarthritis is usually monoarticular or oligoarticular with fluctuations in intensity and localisation over time. It is therefore logical to consider local therapeutic modalities in order to avoid untoward systemic effects. Several compounds have been used intra-articularly (e.g., glucocorticoids, hyaluronic acid) or topically (e.g., capsaicin, methylsalicylate). However, the benefit of intra-articular glucocorticoides lasts only a few days (Barron, M. C., 2007, J. Am. Osteopath., 107, ES21-27).

Polysaccharides form a class of materials whose recognition of the potential utility is growing. Apart from their biological activity, one of the most important properties of polysaccharides in general is their ability to form hydrogels. Hydrogel formation can occur by a number of mechanisms and is strongly influenced by the types of monosaccharide involved, as well as the presence and nature of substituent groups. Polysaccharide gel formation is generally of two types: hydrogen bonded and ionic. Hydrogen-bonded gels are typical of molecules such as agarose (thermal gellation) and chitosan (pH-dependent gellation), whereas ionically bonded gels are characteristic of alginates and carrageenans.

Proteoglycans are one of the major macromolecules found in articular cartilage. These molecules consist of a core protein and covalently attached glycosaminoglycans (GAG) chains. The GAGs are long, unbranched heteropolysaccharides, consisting of repeated disaccharide units, with the general structure: Muronic acid amino sugar. The cartilage-specific GAGs include chondroitin 4-sulfate (glucuronic acid and N-acetyl-galactosamine with an $SO_4$ on the 4-carbon position), chondroitin 6-sulfate (glucuronic acid and N-acetyl-galactosamine with an $SO_4$ on the 6-carbon position) and keratan sulfate (galactose and N-acetyl-glucosamine with an $SO_4$ on the 6-carbon position).

These molecules are capable of forming hydrogel complexes with oppositely charged ionic polymers, particularly the cationic polysaccharide chitosan. This interaction may form the basis of a new materials approach to cartilage tissue engineering. The other important cartilage GAG is hyaluronic acid (glucuronic acid and N-acetyl-glucosamine). This molecule is one of the major components in synovial fluid. Hyaluronic acid molecules are also present in cartilage matrix as the backbone structure in proteoglycan aggregates. In general, hyaluronic acid plays a major role as an organizer of the extracellular matrix. Purified hyaluronic acid is employed as a structural biomaterial because of its high molecular weight and gel forming ability. The properties of the molecule may be broadly altered by chemical modification. For example, partial esterification of the carboxyl groups reduces the water solubility of the polymer and increases its viscosity. Extensive esterification generates materials that form water-insoluble films or swellable gels. Ethyl and benzyl esterified hyaluronate membranes have excellent healing responses and biodegradability properties. The fully esterified membranes have in vivo lifetimes of several months, whereas the partially esterified forms have been shown to degrade within a few weeks.

Hyaluronic acid is responsible for the viscoelastic quality of synovial fluid that acts as both a lubricant and shock absorber. In synovial fluid, hyaluronic acid coats the surface of the articular cartilage and shares space deeper in the cartilage among collagen fibrils and sulfated proteoglycans. It protects the cartilage and blocks the loss of proteoglycans from the cartilage matrix into the synovial space, maintaining the normal cartilage matrix. In synovial fluid from knee joints in osteoarthritis, concentrations of hyaluronic acid, glycosaminoglycans, and keratan sulfate are lower than in synovial fluid from normal knee joints. Additionally, experiments using rabbit synovial cells showed that the proinflammatory cytokines IL-1 and TNF-alpha stimulate the expression of hyaluronic acid synthetase, which may contribute to the fragmentation of hyaluronic acid under inflammatory conditions. Exogenous hyaluronic acid may facilitate the production of newly synthesized hyaluronic acid. Hyaluronic acid and derivatives have been used as therapeutic aids in the treatment of osteoarthritis as a means of improving lubrication of articulating surfaces and thus reducing joint pain. Several in vitro culture studies have also demonstrated that hyaluronic acid has a beneficial effect by inhibiting chondrocytic chondrolysis mediated by fibronectin fragment. Hyaluronic acid has also been shown to have anti-inflammatory effects, as well as inhibitory effects on prostaglandin synthesis, and proteoglycan release and degradation.

Chitosan, a partially de-acetylated derivative of chitin, found in arthropod exoskeletons is another proteoglycan, a linear polysaccharide consisting of beta (1-4) linked D-glucosamine residues with a variable number of randomly located N-acetyl-glucosamine groups. It thus shares some characteristics with various GAGs and hyaluronic acid present in articular cartilage, Depending on the source and preparation procedure, chitosan's average molecular weight may range from about 50 to about 1000 kDa. Commercially available preparations have degrees of deacetylation ranging from about 50 to about 90%. Chitosan is a semi-crystalline polymer and the degree of crystallinity is a function of the degree of deacetylation. Crystallinity is maximum for both chitin (i.e. 0% deacetylated) and fully deacetylated (i.e. 100%) chitosan. Minimum crystallinity is achieved at intermediate degrees of deacetylation.

Much of the potential of chitosan as a biomaterial stems from its cationic nature and high charge density. The charge density allows chitosan to form insoluble ionic complexes or complex coacervates with a wide variety of water-soluble anionic polymers.

In fact, chitosan oligosaccharides have been shown to have a stimulatory effect on macrophages, and the effect has been linked to the acetylated residues. Furthermore, both chitosan and its parent molecule, chitin, have been shown to exert chemoattractive effects on neutrophils in vitro and in vivo. In vivo, chitosan is degraded by enzymatic hydrolysis. The mechanical properties of chitosan scaffolds are mainly dependent on the pore sizes and pore orientations.

Hyaluronic acid, a glycosaminoglycan, is widely used for the treatment of osteoarthritis of the knee. A survey of 2 general practices in the United Kingdom showed that about 15% of patients with osteoarthritis received intra-articular treatment with hyaluronic acid preparations. Because of its viscoelastic quality, it may replace synovial fluid. Furthermore, it may reduce the perception of pain. Beneficial molecular and cellular effects have also been reported. Hyaluronic acid is frequently applied by intra-articular injection, but the evidence concerning its clinical relevance is conflicting. State-of-the-art systematic reviews and meta-analyses were published recently, and their authors concluded that intra-articular hyaluronic acid, at best, has a small effect, a clinically meaningful effect meaning an improvement of at least 15 mm on the visual analog scale of pain (Bellamy et al, 2006; Cochrane Database Syst Rev. 2006 Apr. 19; (2): CD005321). These data form the basis for the use of intra-articular administration of hyaluronic acid in patients with osteoarthritis. The benefits are sometimes noticed only one year after injections and, in some experiments, injections must be performed three to five-times a week (Barron, M. C., 2007, J. Am. Osteopath., 107, ES21-27).

Alpha-2-adrenergic receptor ligands especially agonists are drugs commonly used in medical practice as antihypertensive substance and in clinical anesthesiology as component of general and locoregional anesthesia and analgesia. They produce anxiolysis, analgesia, sedation, anesthetic sparing effects and peri-operative hemodynamic stabilizing effects. Negative neurotoxicity studies allow their use (mainly clonidine) by systemic and perimedullar routes and for peripheral nerve blocks. Among the clinically available alpha-2-adrenoreceptors agonists, clonidine remains widely used: the substance is devoid of neurotoxicity and displays less side effects (i.e. hypotension and sedation) than the more potent and also more alpha-2-adrenergic receptor selective agonist, dexmedetomidine. Clonidine, a potent alpha-2-adrenergic receptors partial agonist, was used primarily for the treatment of hypertension. This drug stimulates alpha-2-adrenergic receptors in the vasomotor centers, causing a reduction of sympathetic outflow from the central nervous system. Both cardiac output and peripheral resistance are reduced resulting in a decrease in blood pressure. Higher concentrations cause a vasoconstriction by activation of postsynaptic receptors in vascular smooth muscle. However, the significant advantages of the drug are counter balanced by side effects including dryness of the mouth, sedation and dizziness. Furthermore, other activities of these compounds such as anti-inflammatory effect have never been reported by oral administration.

Besides the well-known analgesic effects of spinally administered alpha-2-adrenergic (alpha-2-adrenoceptors) agonists, their peripheral use has been commonly reported in acute pain conditions. For peri-operative analgesic techniques, clonidine is added to local anaesthetic in peritroncular nerve blocks to enhance potency and duration of analgesia. ZOUHER A et al.; Paediatr Anaesth. 2005 November; 15(11):964-70; Luiz-Cleber P. et al.; Anesth Analg. 2005 September; 101(3):807-11, Murphy D R "A non-surgical approach to low back pain" Med. Health R. I., 2000 April; 83(4): 104-7). Further, intra-articular injection of clonidine and its adjunction to local anaesthetic solution for intravenous regional anaesthesia have also displayed anti-nociceptive effect S. Armand et al; Br J Anaesth. 1998 August; 81(2):126-34; Gentili M, et al. Pain 1996; 64: 593-596; Reuben S, et al. Anesthesiol. 1999; 91: 654-658. However, the effect is here designed not to last for days or weeks.

Alpha-2-adrenoceptors agonists are known to block the tissue content increase of pro-inflammatory cytokines, such as TNF-alpha and IL-1beta and increase the tissue content of anti-inflammatory cytokine TGF beta. This has been shown in inflammatory neuropathic pain model by partial ligation of sciatic nerve, by applying locally alpha 2 adrenergic receptor agonists by peripheral nerve block.

SUMMARY OF THE INVENTION

The invention is related to a new (intra-articular) pharmaceutical composition for use in the treatment and/or the prevention of acute or chronic osteoarticular diseases and acute or chronic osteoarticular symptoms especially osteoarthritis, this composition comprising
  possibly an adequate pharmaceutical carrier or diluent
  a polysaccharide and/or a glycosaminoglycan, preferably a glycosaminoglycan (including proteoglycan),
  stem cells (differentiated or not), but with the provisio that these stem cells are not human embryonic stem cells, having potential anti-inflammatory properties and
  a sufficient amount of an anti-inflammatory agent (compound).

In the pharmaceutical composition of the invention the polysaccharide or the glycosaminoglycan (including the proteoglycan) are present as a film or a matrix, preferably in the form of a paste or a gel, more preferably an hydrogel with a sufficient amount of an aqueous solvent.

Preferably, the anti-inflammatory agent (compound) is selected from the group consisting of a steroidal (prednisolone, dexamethasone, betamethasone, triamcinolone . . . ), a non-steroidal anti-inflammatory compound (ibuprofen, diclofenac, naproxen, cox-2 inhibitors etc. . . . ), a disease modifying antirheumatic drug (DMARD such as methotrexate, leflunomide, etc. . . . ), an alpha 2 adrenergic receptor agonist, an anti-CD20 agent, an anti-cytokine agent (anti-IL1, anti-IL6, anti-IL17), an anti-TNF agent (infliximab, etanercept, adalimumab, rituximab, etc) or a mixture thereof.

Advantageously, the anti-inflammatory compound is a compound interacting with the alpha-2-adrenergic receptor, preferably an alpha-2-adrenergic receptor agonist.

The alpha-2-adrenergic receptor agonist is selected from the group consisting of clonidine, p-aminoclonidine, tiamenidine, 5-bromo-6-(2 imidazolidine-2-ylamino) quinoxaline, dexmedetomidine, detomidine, medetomidine, alphamethyldopa, oxymetazonline, brimonidine, tizanidine, mivazerol, lofexidine, xylazine, guanfacine, guanclofine, guanoxabenz, or a derivative or structural analogue thereof, alpha-methyl-norepherine, azepexole, indoramin, 6-allyl-2-amino-5,6,7,8-tetrahydro4H-thiazolo [4,5-d]azepine diHCl or a compound identified in the table 1.

In the composition according to the invention the polysaccharide-based hydrogel and the glycosaminoglycan are not covalently linked or are covalently linked.

Preferably, the glycosaminoglycan is selected from the group consisting of hyaluronic acid with low (<900 kDa) or high (>900 kDa) molecular mass.

In the composition of the invention, the hyaluronic acid and the alpha 2 adrenergic receptor agonist are not covalently linked or are covalently linked.

In the composition according to the invention the glycosaminoglycan is selected from the group consisting of proteoglycan, chondroitin sulfate, keratin sulphate, hyaluronic acid, (including their derivative), chitosan, a chitosan or chitin derivative, or a mixture thereof.

Advantageously, the non human embryonic stem cells of the composition are selected from the group consisting of (cells obtained from) bone marrow or adipose tissue or bone tissue or joint tissue, a mix of hematopoietic and mesenchymal stromal cells, (expanded or not), mesenchymal stromal cells, osteoblastic cells, chondrocytic cells or a combination thereof.

The inventors have discovered that the pharmaceutical composition according to the invention is suitable for a treatment or prevention of acute and/or chronic osteoarticular diseases and associated symptoms (especially osteoarticular pain, mobility or function), of inflammatory origin, such as osteoarthritis, degenerative arthristis, degenerative arthritis, gonarthrosis, coxarthrosis, and other inflammatory general conditions in which joints are involved, such as autoimmune diseases, especially rheumatoid arthritis and systemic lupus erythematosus (SLE) spondyloarthropathies, polymyalgia rheumatica, ankylosing spondylitis, Reiter's Syndrome, psoriatic arthropathy, enteropathic arthritis (related to inflammatory bowel disease, such as haemorrhagic colitis and Crohn's disease), neuropathic arthropathy, acute rheumatic fever, gout, chondrocalcinosis, calcium hydroxyapatite crystal deposition disease, Lyme disease and all other degenerative joint diseases.

The composition of the invention is also suitable for obtaining an efficient proliferation of stem cells therefore, for improving regenerative or damaged tissues. This effect upon regeneration of treated tissues is advantageously induced by the synergic effect of the active compounds present in the composition of the invention.

Therefore, the composition according to the invention is characterized by an anti-inflammatory activity, a tissue or cell regenerative effect, and an advantageous efficient treatment and/or prevention of acute and/or chronic osteoarticular diseases and/or symptoms. These effects could be combined in the composition according to the invention.

According to a preferred embodiment of the present invention the composition presents a preferred formulation, preferably being an injectable solution for delivering an efficient amount (therapeutic dose) of the active compound present in the composition to a mammal subject including a human patient, especially in the knees, the hips and the spine of the subject.

Preferably, this injectable solution comprises from about 0.1 mg to about 100 mg/kg preferably from about 1 mg to about 10 mg/kg of body weight of this polysaccharide and/or glycosaminoglycan, preferably in the form of a polysaccharide-based hydrogel and may comprise from about 0.1 mg to about 100 mg/kg of patient body weight preferably from about 0.1 mg to about 0.8 mg/kg of patient body weight of an anti-inflammatory compound, being preferably a compound activating the alpha-2-adrenergic receptor, preferably an alpha-2-adrenergic receptor agonist.

The injectable solution is adequate for intra-articular administration (percutaneous injection) in a joint of a mammal subject, preferably of a human patient.

This formulation is also adequate for local administration (percutaneous injection in/or in the vicinity of an inflamed joint of a mammal subject, preferably of a human patient), local administration injection that does concern the epidermis, the muscle or any deep organs.

Another aspect of the present invention is related to the use of the pharmaceutical composition for the manufacture of a medicament in the treatment and/or the prevention of these mentioned diseases and/or symptoms (pain) induced by these diseases.

The present invention is related to the surprising discovery that this intra-articular administration to a mammal subject, particularly a human patient of this pharmaceutical composition results in an improvement of symptoms associated with osteoarticular diseases, such as a relief of osteoarticular pain, an improvement of joint mobility and/or function, a decrease in articular accumulation of inflammatory liquid, induced by the above mentioned diseases or pathologies.

The present invention is also related to the surprising discovery that the intra-articular administration to a mammal subject, particularly a human patient of the pharmaceutical composition according to the invention results in both a reduction of inflammation, and of joint degeneration, resulting in disease improvement and joint regenerative effects, combined with the above effects in the improvement of symptoms associated with osteoarticular diseases. These effects are obtained by the synergic combination of the elements present in the composition.

The present invention is also related to the surprising discovery that the intra-articular administration to a mammal subject, particularly a human patient of the pharmaceutical composition according to the invention results also in a shortening of the time to onset of the therapeutic activity of the first component, an increase in the duration of action of the first component.

The composition and method of the present invention also allows a decrease of the number of required administrations to obtain a desired efficacy and allows for a faster onset of action.

The invention is also directed to a method for a treatment and/or a prevention (prophylaxis) of a condition selected from the group consisting of the above mentioned diseases or symptoms through an administration to a mammal subject, preferably a human patient of a sufficient amount of the pharmaceutical composition of the invention, through an intra-articular administration, particularly in the knees, the hips and the spine or any joint (e.g., interphalangeal) of the mammal subject; preferably the human patient.

A last aspect of the present invention is related to a kit of parts comprising one or more vials with the elements (carrier/diluent, polysaccharide, glycosaminoglycan, anti-inflammatory agent (or compound), stem cells or a combination thereof) of the composition of the invention and a device for delivering these elements (simultaneously or successively) or this composition to an inflamed joint of a mammal subject, preferably a human patient suffering from the above mentioned osteoarticular diseases or symptoms (in particular pain) and having
    reservoir means for storing this pharmaceutical composition,
    piston means movable along the longitudinal axis of the reservoir for dispensing this pharmaceutical composition and,
    a hollow needle mounted on said reservoir means for delivering this pharmaceutical composition to the peripheral nerve of the mammal subject.

These and other objects and features of the invention will become more fully apparent when the following detailed description of the invention is read in conjunction with the accompanying example.

DETAILED DESCRIPTION OF THE INVENTION

The term "intra-articular" as used herein refers to a percutaneous injection of a joint with the pharmaceutical composition of the invention.

The term "local administration" as used herein refers to a percutaneous injection in or in the vicinity of an inflamed joint. Local administration injection thus concerns the epidermis, the dermis, the muscle, or any deep organ.

The main advantages to local administration are to selectively restrict the analgesic effect to the injured areas. Furthermore, the local administration allows for high local concentration levels with little or no systemic release. The local administration and the intra-articular injection of hyaluronic acid is a recognised treatment of the above mentioned conditions.

The local administration and the intra-articular injection of the anti-inflammatory compound and stem cells are easily realizable and provide long lasting effect in combination with proteoglycans. In consequence, the problems related to placement of an invasive drug delivery system and the problems of bothersome side-effects, due to systemic release, can be strongly minimized. Health-related quality of life, patient satisfaction and economic assessment might be improved with such a treatment, especially in chronic conditions.

Preferably, the administrated proteoglycan is selected from the group consisting of a polysaccharide-based hydrogel or a glycosaminoglycan, for example hyaluronic acid or a salt thereof or an ester of hyaluronic acid with an alcohol of the aliphatic, heterocyclic or cycloaliphatic series, or a sulphated form of hyaluronic acid or combination of agents containing hyaluronic acid. Suitable dosages of a polysaccharide-based hydrogel or a glycosaminoglycan or a derivative thereof will typically be from about 0.1 mg to about 100 mg/kg body weight per day or from about 0.5 mg to about 10 mg/kg body weight per day more preferably from about 2 mg to about 8 mg by body weight per day.

Advantageously, the administrated stem cells are from bone marrow, adipose tissue, bone tissue or joint tissue, composed of a mix of hematopoietic and mesenchymal stromal cells, of mesenchymal stromal cells—expanded or not, of osteoblastic cells or chondrocytic cells or any combination thereof.

According to a first embodiment, the administrated stem cells are osteoblastic cells, or preferably a cell population selected from the group consisting of osteoprogenitors, pre-osteoblasts and osteoblasts.

According to the second embodiment, the administrated stem cells are chondrocytic cells, or even preferably a cells population selected from the group consisting of chondroprogenitors, pre-chondrocytes and chondrocytes.

In a preferred embodiment, the alpha 2 adrenergic receptor agonist may be clonidine, p-aminoclonidine, tiamenidine, 5-bromo-6-(2 imidazolidine-2-ylamino) quinoxaline, dexmedetomidine, detomidine, medetomidine, alphamethyldopa, oxymetazonline, brimonidine, tizanidine, mivazerol, lofexidine, xylazine, guanabenz, guanfacine, guanclofine, guanoxabenz, or a derivative or structural analogue thereof, alpha-methylnorepherine, azepexole, indoramin, 6-allyl-2-amino-5,6,7,8-tetrahydro4H-thiazolo[4,5-d]azepine diHCl analogs thereof or a compound selected from the table 1 and analogs thereof.

TABLE 1

Classification of the alpha-2-adrenergic receptor agonists guanidines agmatine
betanidine
biguanides
cimetidine
creatine
gabexate
guanethidine
guanfacine
guanidine
impromidine
iodo-3 benzylguanidine
methylguanidine
mitoguazone
nitrosoguanidines
pinacidil
robenidine
sulfaguanidine
zanamivir
imidazoles 4-(3-butoxy-4-méthoxybenzyl)imidazolidin-2-one
acide urocanique
amino-imidazole carboxamide
antazoline
biotine
bis(4-methyl-1-homo piperazinylthiocarbonyl)disulfide
carbimazole
cimetidine
clotrimazole
creatinine
dacarbazine
dexmedetomidine
econazole
enoximone
ethymizol
etomidate
fadrozole
fluspirilène
histamine
histidinol
idazoxan
imidazolidines imidazolines
clonidine
tolazoline
impromidine
levamisole
losartane
medetomidine
miconazole
naphazoline
niridazole
nitroimidazoles
ondansetron
oxymetazoline
phentolamine
tetramisole
thiamazole
trimetaphan TABLE 1-continued Classification of the alpha-2-adrenergic receptor agonists Derivatives of clonidine 2,6-dimethylclonidine
4-azidoclonidine
4-carboxyclonidine-methyl 3,5-dichlorotyrosine
4-hydroxyclonidine
4-iodoclonidine
alinidine
apraclonidine
chlorethylclonidine
clonidine 4-isothiocyanate
clonidine 4-methylisothiocyanate
clonidine receptor
clonidine-displacing substance
hydroxyphenacetyl aminoclonidine
N,N'-dimethylclonidine The active compounds used in accordance with the invention are known. Pharmaceutical preparations containing hyaluronic acid are commercially available as are clonidine and other alpha 2 adrenergic receptor agonists. The compounds can be manufactured in a known manner essentially in accordance with the processes described in the prior art.

The term "clonidine" as used herein refers to N-(2,6-dichlorophenyl)-4,5-dihydro-1H-imidazol-2-amine and includes the pharmaceutically acceptable salts thereof, e.g., salts with inorganic acids, such as hydrohalic acids, or with organic acids, for example lower aliphatic monocarboxylic or dicarboxylic acids such as acetic acid, fumaric acid or tartaric acid or aromatic carboxylic acids such as salicylic acid are also suitable.

Clonidine is employed in a therapeutically effective amount. The present invention also encompasses the use of alpha 2 adrenergic receptor agonist for the manufacture of injectable formulations for a delivery to a joint or a close region thereof, a therapeutic dose of said agonist by intra-articular injection, wherein said solution comprises from about 3 μg to about 1500 μg of said alpha 2 adrenergic receptor agonist. Preferably, said formulation comprises from about 30 μg to about 500 μg of said alpha 2 adrenergic receptor agonist. More preferably said solution comprises from 50 μg to 350 μg of said alpha 2 adrenergic receptor agonist. In a preferred embodiment, the alpha 2 adrenergic receptor agonist is clonidine. The actual concentration of clonidine may vary, depending on the nature and degree of the pain syndromes being treated and whether the drug is being administered for therapeutic or prophylactic purposes.

It is hypothesized that based on their anti-inflammatory properties, inhibition of pro-inflammatory cytokines TNF-alpha and IL1-beta and the increase of anti-inflammatory cytokines such as TGF beta, alpha 2 receptor agonists in injectable administration will have applications in osteoarticular inflammatory conditions and in diseases where there are osteoarticular inflammatory conditions, such as those above mentioned.

According to the method and the formulation of the invention, an injection of the combination of hyaluronic acid and an alpha 2 adrenergic receptor agonist form induces a long lasting pain relief, both in human case and in an animal model of osteoarticular pain. The method is safe, devoid of major drug's side effects and allows for acute as well as chronic treatment and or prophylaxis without the use of too invasive technique.

Preservatives may be incorporated in an amount effective for inhibiting growth of microbes, such as bacteria, yeast and molds, in the composition. Any conventional preservative against microbial contamination of the product can be employed so long as it is pharmaceutically acceptable and is unreactive with clonidine. Preferred preservatives are antimicrobial aromatic alcohols, such as benzyl alcohol, phenoxyethanol, phenethyl alcohol, and the like, and esters of parahydroxybenzoic acid commonly referred to as paraben compounds, such as methyl, ethyl, propyl, and butyl esters of parahydroxybenzoic acid and the like and mixtures thereof, but are not limited thereto. Particularly preferred are benzyl alcohol and phenoxyethanol.

Optionally, anaesthetic agent, such as lidocaine and the like, can be included. For administration according to the invention the active quantities of the compounds that alleviate neuropathic pain can be contained together with customary pharmaceutical excipients and/or additives in solid or liquid pharmaceutical formulations.

Liquid preparations such as solutions, suspensions or emulsions of the active ingredients, prepared by dissolving or dispersing the compounds, can contain the usual diluents such as water, oil and/or suspending aids such as polyethylene glycols and optional pharmaceutical adjuvants, in a carrier, such as, for example, aqueous saline, aqueous dextrose, glycerol, or ethanol, to form a solution or suspension and such like. Further additives such as preservatives, flavouring agents and such like may also be added.

EXAMPLE

The effects of the combination of alpha 2 adrenoreceptor agonists (e.g., clonidine), of a glycosaminoglycan (e.g., hyaluronic acid) and of stem cells were tested in an inflammation model with stimulated Peripheral Blood Mononuclear Cells.

PBMCs (Peripheral blood mononuclear cells) from heparinized venous blood of healthy volunteers were isolated by Ficoll-gradient centrifugation. MNC (Mononuclear cells) were washed three times in PBS and resuspended in RPMI-1640 medium supplemented with 100 U/mL penicillin, 100 µg/mL streptomycin, and 10% heat-inactivated FBS (Fetal Bovine Serum). Cells were seeded at 100.000 cells in 96-wel plate in a total volume of 200 µL/well.

PBMC, at 100.000 cells/200 µL, were plated in 96-well microtiter plates and stimulated or not with 10 µg/mL phytohemagglutinin (PHA). Effects of hyaluronic acid "HA" (200 µg/mL) and p-aminoclonidine "A2A" (5 µM) were tested on PBMC.

MSC (Mesenchymal stromal cells) were derived from 20 to 60 mL of heparinized bone marrow (BM) obtained from the iliac crest of healthy volunteers. BM was mixed with phosphate-buffered saline (PBS, 2v:v) and layered on density gradient Ficoll solution. After centrifugation, mononuclear cells were harvested from the interface and washed twice in PBS. Cells were resuspended in standard MEM medium supplemented with 15% FBS. The cells were plated at $2 \times 10^6$ cells/75 cm2 flasks and maintained in a 37° C. humidified atmosphere containing 5% CO2. Cells were allowed to attach for 24 hours prior an initial medium change. Cells were detached at day 10 using trypsin-EDTA solution for 1-5 min at 37° C. Then, cells were irradiated (10 minutes at 2200Ci) before seeding in 96-well for proliferative assays at 12.500 cells/well to obtain a ratio 1:8 (MSC:PBMC).

Proliferation Assay

The culture was incubated with 1 µCi/mL 3H-thymidine for 24 hours before end of culture to measure the proliferation. Then, cells were washed twice with ice-cold PBS and twice with ice-cold 5% trichloroacetic acid (TCA). Finally, cells were lysed with 0.1N NaOH-0.1% Triton-X100. Supernatants were collected and analyzed on a beta-counter in presence of scintillation liquid. Results were done in cpm ("count per minute"=disintegration number of radioactive element observed in series of successive counts of one minute). IL-1β (beta) detection (By ELISA). Levels of IL-1β from PBMC or culture supernatants were measured by Quantikine ELISA kit (R&D Systems Inc, Mineapolis, USA). The minimum detectable concentration of IL-1β was estimated at 1.0 pg/mL.

The release of IL-1 beta by PBMC and the proliferation of PBMC, induced by PHA stimulation, were set as controls, and compared with the measures for PBMC treated with HA and/or A2A.

The inhibition of PBMC release of IL-1beta and the inhibition of PBMC proliferation, induced by LPS stimulation of TH1 cells, were also measured and provided similar trends as for PHA stimulated cells.

Effects of HA Alone

| Conditions tested | IL-1β detection (pg/mL) | Proliferation (cpm) |
|---|---|---|
| PBMC | ND* | 769 |
| PBMC + PHA | 2185 | 16069 |
| PBMC + HA | 2095 | 364 |
| PBMC + PHA + HA | 6394 | 9087 |

*not determined

| Conditions tested | IL-1β detection (%) | Proliferation (%) |
|---|---|---|
| PBMC | ND* | 5 |
| PBMC + PHA | 100 | 100 |
| PBMC + HA | 96 | 2.2 |
| PBMC + PHA + HA | 293 | 57 |

*not determined

IL-1beta secretion induced by PHA stimulation shows a significant increase over basal condition (where IL-1beta levels were undetectable) and was set at 100. Proliferation of PMBC cells also significantly increased, by a factor of about 20. Surprisingly, a similar cytokine increase (over basal condition) was observed with addition of HA alone, while PBMC proliferation was not affected. When stimulated by PHA, the addition of HA synergistically increases IL-1beta secretion, 3 times over the stimulated conditions, but was able to reduce PBMC proliferation by a factor 2.

Effects of A2A Alone

| Conditions tested | IL-1β detection (pg/mL) | Proliferation (cpm) |
|---|---|---|
| PBMC | ND* | 769 |
| PBMC + A2A | ND* | 786 |
| PBMC + PHA | 2185 | 16069 |
| PBMC + PHA + A2A | ND* | 16212 |

| Conditions tested | IL-1β detection (%) | Proliferation (%) |
|---|---|---|
| PBMC | ND* | 5 |
| PBMC + A2A | ND* | 4.9 |
| PBMC + PHA | 100 | 100 |
| PBMC + PHA + A2A | ND* | 101 |

*not determined

A2A had no effect on basal (unstimulated) conditions. Interestingly, when stimulated by PHA, the addition of A2A totally suppressed the increase in IL-1beta secretion due to PHA stimulation, to undetectable levels, but was not able to inhibit PBMC proliferation.

Effects of Combination of A2A & HA

| Conditions tested | IL-1β detection (pg/mL) | Proliferation (cpm) |
| --- | --- | --- |
| PBMC + PHA | 2185 | 16069 |
| PBMC + PHA + HA | 6394 | 9087 |
| PBMC + PHA + HA + A2A | 3053 | 5445 |

*not determined

| Conditions tested | IL-1β detection (%) | Proliferation (%) |
| --- | --- | --- |
| PBMC + PHA | 100 | 100 |
| PBMC + PHA + HA | 292 | 57 |
| PBMC + PHA + HA + A2A | 139 | 34 |

*not determined

Interestingly, the combination HA/A2A demonstrates a potent anti-inflammatory effect over the PHA/HA condition. Indeed, the addition of A2A was able to significantly revert (by over 50%) the increase in IL-1beta secretion due to PHA/HA stimulation, bringing its level to the one of the PHA alone condition. Surprisingly, A2A was further able to inhibit PBMC proliferation, by another 35%.

Effects of MSC Addition

Testing the effects of MSC on both PBMC-proliferation and IL-1β secretion, a stimulatory effect was observed over basal (unstimulated) conditions. Surprisingly, the proliferative effect was maintained in stimulated conditions (e.g., presence of PHA), but instead of a pro-inflammatory effect on IL-1β secretion, a potent inhibitory effect was observed (−62%).

| Conditions tested | IL-1β detection (pg/mL) | Proliferation (cpm) |
| --- | --- | --- |
| PBMC | ND* | 769 |
| PBMC + MSC | 229 | 1612 |
| PBMC + PHA | 2185 | 16069 |
| PBMC + PHA + MSC | 841 | 26192 |

*not determined

| Conditions tested | IL-1β detection (%) | Proliferation (%) |
| --- | --- | --- |
| PBMC | ND* | 100 |
| PBMC + MSC | +++ | 209 |
| PBMC + PHA | 100 | 100 |
| PBMC + PHA + MSC | 38 | 163 |

*not determined

In PHA stimulated conditions and in presence of hyaluronic acid, MSCs were modestly (about 10%) anti-inflammatory and anti-proliferative.

| Conditions tested | IL-1β detection (pg/mL) | Proliferation (cpm) |
| --- | --- | --- |
| PBMC | ND* | 769 |
| PBMC + PHA | 2185 | 16069 |
| PBMC + PHA + HA | 6394 | 9087 |
| PBMC + PHA + HA + MSC | 5769 | 8673 |

*not determined

| Conditions tested | IL-1β detection (%) | Proliferation (%) |
| --- | --- | --- |
| PBMC | ND* | 5 |
| PBMC + PHA | 100 | 100 |
| PBMC + PHA + HA | 292 | 57 |
| PBMC + PHA + HA + MSC | 264 | 54 |

*not determined

Finally in PHA stimulated conditions and in presence of A2A, MSCs had no influence.

| Conditions tested | IL-1β detection (pg/mL) | Proliferation (cpm) |
| --- | --- | --- |
| PBMC | ND* | 769 |
| PBMC + PHA | 2185 | 16069 |
| PBMC + PHA + A2A | ND | 16212 |
| PBMC + PHA + A2A + MSC | 314 | 17061 |

*not determined

| Conditions tested | IL-1β detection (%) | Proliferation (%) |
| --- | --- | --- |
| PBMC | ND* | 5 |
| PBMC + PHA | 100 | 100 |
| PBMC + PHA + A2A | ND | 100 |
| PBMC + PHA + A2A + MSC | 14 | 106 |

*not determined

During inflammation, lower molecular weight fragments of hyaluronan are known to be inflammatory and immune-stimulatory agents by inducing the secretion of cytokines such as IL-6 and monocyte chemoattractant protein (MCP-1). HA has also the property to enhance the adhesion of lymphocytes and monocytes to the extracellular matrix (Yamawaki et al., 2009). The present experiments show that hyaluronic acid has a potent stimulatory effect on cytokine (e.g., IL-1β) production without PBMC proliferation.

It has been demonstrated that clonidine alters the Th1/Th2 cytokine production (Xu et al., 2007; Cook-Mills et al., 1995). The present experiments show that the addition of alpha 2 adrenoreceptor agonists totally suppresses the increase in cytokine (e.g., IL-1beta) secretion due to PHA stimulation, but is not able to inhibit PBMC proliferation.

Surprisingly, the combination HA/A2A demonstrates a potent anti-inflammatory effect both on cytokine production and inflammatory cell proliferation. Indeed, the addition of A2A to HA was able to significantly inhibit the increase in IL-1beta secretion and was further able to inhibit PBMC proliferation.

An in vitro property of MSCs is their ability to reduce the proliferation of lymphocytes of various types while enjoying immune privilege in vitro and in vivo (Bocelli-Tyndall et al., 2007). However, it was shown that the number of MSCs and the incubation time were key factors in MSCs' lymphocyte regulation: inhibition of lymphocyte proliferation was dose-dependent on MSC concentrations (LeBlanc in 2003).

Figure 1:
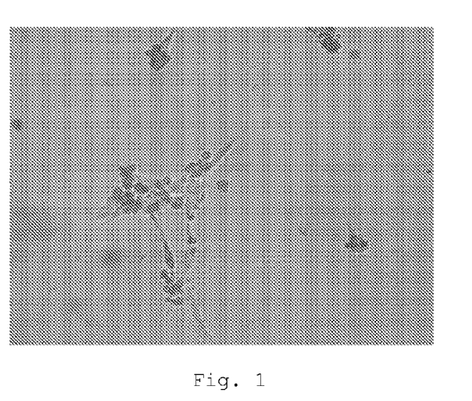
FIG. 1 shows the attachment of peripheral blood mononuclear cells (PBMCs) on the surface of mesenchymal stromal cells (MSCs).

Interestingly, these results show that MSC have a moderate stimulatory effect on unstimulated PBMC by increasing both IL-1beta secretion and increase PBMC proliferation. On the contrary, MSC displayed a potent anti-inflammatory effect (−62%) on IL-1beta secretion but increased PBMC proliferation. The inventors have hypothesized that MSCs did not induce proliferation of PBMC, but were able to increase their survival rate. This is illustrated by the attachment of PBMCs on the surface of MSCs (see enclosed FIG. 1). This seems to be confirmed by the increase in viability observed with PHA stimulated PBMCs in presence of MSCs; a viability increased by over 20%.

Regenerative Effects

MSCs were culture in chondrogenic medium for 7, 14 and 21 days and 4 conditions were tested
control
A2A: 5 µMol aminoclonidine
HA: 200 µg/ml of hyaluronic acid
HA+A2A: 200 µg/ml of hyaluronic acid and 5 µMol aminoclonidine At day 14 and 21, pellets were fixed in 10% buffered formalin for 6 hours, and washed twice in PBS. Pellets were then embedded in OCT (Sakura Finetek, Belgium). Sections were cut at a thickness of 5 µm and were stained with Alcian blue, before counterstained with Nuclear fast red (Klinipath, Belgium)

Alcian blue is one of the most widely used cationic dyes for the demonstration of glycosaminoglycans (GAGs). GAGs will be stained blue, while Nuclear fast red will counterstain cells nuclei in pink or red, and cytoplasm in pale pink. In brief, the procedure is 1) Stain in alcian blue solution for 30 minutes; 3) Wash in running tap water for 2 minutes; 4) Rinse in distilled water; 5) Counterstain in nuclear fast red solution for 5 minutes; 6) Wash in running tap water for 1 minute; 7) Dehydrate through 95% alcohol, and 2 changes of absolute alcohol, 3 minutes each; 8) clear in Ultraclear, a xylene substitute (Klinipath, Belgium); 9) Mount with Ultrakit mounting medium (Klinipahth, Belgium). Toluidine blue stains proteoglycan in red-purple (metachromatic staining) and the nucleus in blue (orthochromatic staining). Metachromasia, tissue elements staining a different color from the dye solution, is due to the pH, dye concentration and temperature of the basic dye. Blue or violet dyes will show a red color shift, and red dyes will show a yellow color shift with metachromatic tissue elements. Toluidine Blue is an often used to stain proteoglycans and glycosaminoglycans in tissues such as cartilage.

Figure 2:
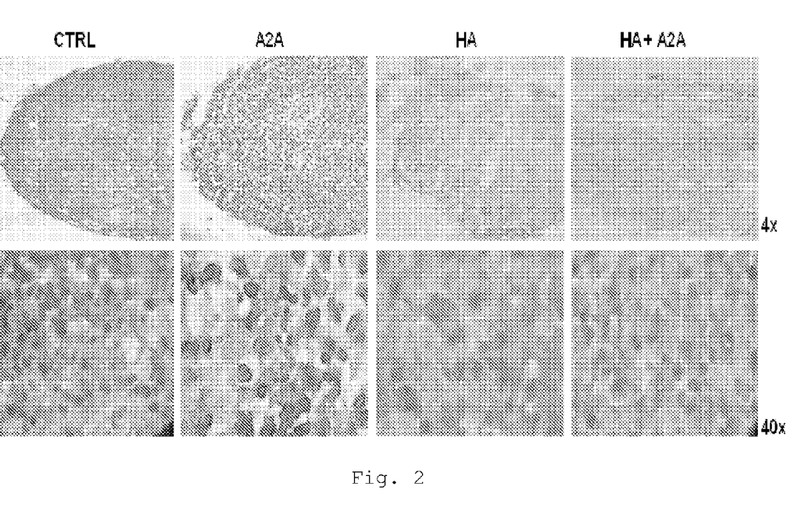
FIG. 2 shows Alcian blue staining of pellets obtained by culturing mesenchymal stromal cells (MSCs) in chondrogenic medium treated with p-aminoclonidine (A2A), hyaluronic acid (HA) or A2A and HA at low magnification power (4x) and high magnification power (40x).

Results. Although pellets from different conditions were of similar size (mean of 0.7 mm; range from 0.9 to 0.4 mm), Alcian Blue staining reveals that cellularity of pellets was significantly affected by the changes in conditions. For example, the addition of hyaluronic acid strongly reduced the cellularity of the pellet. In parallel, matrix (i.e., mucopolysaccharides and glycosaminoglycans) content was almost absent in control and A2A alone conditions as illustrated in FIG. 2 by the absence of blue staining while in the hyaluronic acid and hyaluronic acid/clonidine conditions, the slides were uniformly blue stained, demonstrating an important matrix production. The combined condition HA/A2A appears to further increase the matrix production over HA alone condition.

FIG. 2: Alcian blue staining at low magnification power (Top) and high magnification power (Bottom) for the different culture conditions: control, A2A (clonidine alone), HA (hyaluronic acid alone) and HA/A2A (combination of hyaluronic acid and clonidine)

Interestingly, cell nucleus staining demonstrate that the addition of clonidine (HA/A2A) to hyaluronic acid (HA) increases the cellularity of pellet.

In conclusion, the combination of hyaluronic acid, an anti-inflammatory compound such as an alpha2 adrenoreceptor agonist and mesenchymal stromal cell displays surprisingly synergistic anti-inflammatory and regenerative effects:

The presence of mesenchymal stromal cells are required for the de novo production of cartilage matrix;
This production is significantly increased (and accelerated) by the addition of hyaluronic acid, but the addition of hyaluronic acid has potent pro-inflammatory effects;
These hyaluronic acid potent pro-inflammatory effects are totally neutralized by the addition of alpha2-adrenergic agonists;
The addition of alpha2-adrenergic agonist agents supports the regenerative effects of the combination of mesenchymal stromal cells and hyaluronic acid by increasing the cellularity of the cell preparation and the production of matrix.

REFERENCES

Bocelli-Tyndall et al. (Rheumatology; 46:403-408 (2007)).
Bondeson et al. (Arthritis Res Ther; 8(6):R187 (2006)).
Cook-Mills et al., 1995. (Immunology. 85 544-549 (1995)).
Le Blanc et al., (Scandinavian Journal of Immunology, 57, 11-20 (2003)).
Levesque et al., (The Journal of Immunology, 166: 188-196 (2001)).
Mchugh et al. (Clin Exp Immunol. 99:160-167 (1995)).
Pelletier et al. (Arthritis Rheum. 44(6):1237-47 (2001)).
Yamawaki H et al. (Glycobiology, 19, 83-92 (2009)).

The invention claimed is:

1. A method of treating a chronic osteoarticular disease in a mammalian subject, comprising administering to the subject a pharmaceutical composition comprising:
   an adequate pharmaceutical carrier or diluent;
   a hyaluronic acid, or a hyaluronic derivative selected from a group consisting of: a hyaluronic salt, sulfated hyaluronic acid, or an ester of hyaluronic acid, each of the hyaluronic derivatives optionally comprising an alcohol of the aliphatic, heterocyclic, and cycloaliphatic series;
   an effective amount of an anti-inflammatory compound selected from the group consisting of:
   the alpha 2 adrenergic receptor agonists
   clonidine or p-aminoclonidine;
   the corticosteroid dexamethasone;
   the non-steroidal anti-inflammatories ibuprofen or diclofenac;
   an anti-TNF-alpha antibody; and
   an effective amount of mesenchymal stem cells,
   wherein the pharmaceutical composition reduces joint degeneration in the subject associated with the chronic osteoarticular disease thereby providing clinical improvement of the chronic osteoarticular disease.

2. The method according to claim 1 wherein the pharmaceutical composition is administered to the subject through intra-articular injection.

3. The method according to claim 1 wherein the mesenchymal stem cells are obtained from bone marrow concentrate.

4. The method according to claim 1 which comprises administering an amount of the pharmaceutical composition such that the subject receives from about 0.1 to about 100 mg/kg of body weight of the hyaluronic acid or hyaluronic derivative.

5. The method according to claim 1 which comprises administering an amount of the pharmaceutical composition such that the subject receives from about 0.1 to about 100 mg/kg of body weight of anti-inflammatory compound.

6. The method according to claim 1 wherein an injectable solution is administered to the subject.

7. The method according to claim 6 wherein the injectable solution is administered to the subject twice a week.

8. The method according to claim 6 wherein the injectable solution is administered to the subject once a week.

9. The method according to claim 6 wherein the injectable solution is administered to the subject once in two or three weeks.

10. The method according to claim 1 wherein the osteoarticular disease is osteoarthritis, degenerative arthritis, gonarthrosis, coxarthrosis, gout, chondrocalcinosis, calcium hydroxyapatite crystal deposition disease, spondyloarthropathies, ankylosing spondylitis, Reiter's Syndrome, psoriatic arthropathy, enteropathic arthritis, rheumatoid arthritis, neuropathic arthropathy, or acute rheumatic fever.

11. The method of claim 1, wherein the subject is a human.

12. The method of claim 1, wherein the pharmaceutical composition promotes regeneration of cartilage matrix.

\* \* \* \* \*